(12) United States Patent
Albright et al.

(10) Patent No.: US 9,573,000 B2
(45) Date of Patent: Feb. 21, 2017

(54) HIFU APPLICATOR

(75) Inventors: Ethan P. Albright, Mill Creek, WA (US); Roland Horth, Auckland (NZ); John Murkowski, Seattle, WA (US); Troy Brown, Seattle, WA (US); Daniel B. Phillips, Bellevue, WA (US); Gregory P. Darlington, Snohomish, WA (US); Adam L. Smith, Palm Desert, CA (US); Scott C. Thielman, Seattle, WA (US); Blake R. Stancik, Mukilteo, WA (US)

(73) Assignee: Mirabilis Medica Inc., Bothell, WA (US)

( * ) Notice: Subject to any disclaimer, the term of this patent is extended or adjusted under 35 U.S.C. 154(b) by 667 days.

(21) Appl. No.: 13/213,042

(22) Filed: Aug. 18, 2011

(65) Prior Publication Data
US 2012/0046592 A1    Feb. 23, 2012

Related U.S. Application Data

(60) Provisional application No. 61/375,001, filed on Aug. 18, 2010.

(51) Int. Cl.
*A61H 1/00* (2006.01)
*A61H 1/02* (2006.01)
(Continued)

(52) U.S. Cl.
CPC .............. *A61N 7/02* (2013.01); *G10K 11/355* (2013.01); *A61B 8/00* (2013.01); *A61B 8/429* (2013.01);
(Continued)

(58) Field of Classification Search
USPC .............................. 601/2; 600/437, 439, 447
See application file for complete search history.

(56) References Cited

U.S. PATENT DOCUMENTS 3,470,868 A   10/1969   Krause
3,480,002 A   11/1969   Flaherty
(Continued)

FOREIGN PATENT DOCUMENTS

EP    0 328 943 A1    8/1989
EP    0 734 742 A2    10/1996
(Continued)

OTHER PUBLICATIONS

International Search Report and Written Opinion mailed Mar. 15, 2012, issued in corresponding International Application No. PCT/US2011/048331, filed Aug. 18, 2011, 8 pages.
Chen, L., et al., "Effect of Blood Perfusion on the Ablation of Liver Parenchyma With High-Intensity Focused Ultrasound," Physics in Medicine and Biology 38(11):1661-1673, Nov. 1993.
Cheng, S.-Q., et al., "High-Intensity Focused Ultrasound in the Treatment of Experimental Liver Tumour," Journal of Cancer Research and Clinical Oncology 123(4):219-223, Apr. 1997.
(Continued)

*Primary Examiner* — James Kish
(74) *Attorney, Agent, or Firm* — Seed IP Law Group LLP

(57) ABSTRACT

An applicator for providing HIFU therapy to a patient includes a HIFU transducer that is rotatably coupled to a frame. In one embodiment, the rotatable coupling is configured such that the HIFU transducer can be mechanically oriented to position a focal zone of the HIFU transducer at any desired location in a treatment volume radially outward from a longitudinal axis of the applicator while the HIFU transducer remains within a housing that is not more than a defined percentage (e.g., 50%) larger than the maximum diameter of the HIFU transducer. In one embodiment, the HIFU transducer is rotatably coupled to the frame with a ball and socket joint. In another embodiment, the HIFU transducer is rotatably coupled to the frame with an offset gimble assembly. A pair of linear actuators and drive shafts engage the HIFU transducer to orient HIFU transducer in a desired direction.

26 Claims, 11 Drawing Sheets

(51) Int. Cl.
*A61H 5/00* (2006.01)
*A61N 7/02* (2006.01)
*G10K 11/35* (2006.01)
*A61B 8/00* (2006.01)
*A61N 7/00* (2006.01)

(52) U.S. Cl.
CPC ........ *A61B 8/4461* (2013.01); *A61B 2090/378* (2016.02); *A61N 2007/0091* (2013.01)

(56) References Cited

U.S. PATENT DOCUMENTS

| | | |
|---|---|---|
| 3,676,584 A | 7/1972 | Plakas |
| 4,097,835 A | 6/1978 | Green |
| 4,282,755 A | 8/1981 | Gardineer |
| 4,421,118 A * | 12/1983 | Dow et al. ................ 600/446 |
| 4,579,122 A | 4/1986 | Shimizu et al. |
| 4,756,313 A | 7/1988 | Terwilliger |
| 4,771,787 A * | 9/1988 | Wurster et al. ............. 600/439 |
| 4,817,616 A | 4/1989 | Goldstein |
| 4,819,621 A | 4/1989 | Ueberle |
| 4,858,613 A | 8/1989 | Fry |
| 4,865,042 A * | 9/1989 | Umemura et al. .......... 600/439 |
| 4,893,624 A | 1/1990 | Lele |
| 4,920,966 A * | 5/1990 | Hon et al. ................. 600/459 |
| 4,932,414 A | 6/1990 | Coleman |
| 4,938,217 A | 7/1990 | Lele |
| 4,947,830 A | 8/1990 | Rattner et al. |
| 4,957,099 A * | 9/1990 | Hassler ...................... 601/4 |
| 4,991,604 A * | 2/1991 | Wurster et al. ............. 600/439 |
| 5,005,579 A | 4/1991 | Wurster |
| 5,036,855 A | 8/1991 | Fry |
| 5,070,879 A | 12/1991 | Herres |
| 5,080,101 A | 1/1992 | Dory |
| 5,080,102 A | 1/1992 | Dory |
| 5,095,908 A * | 3/1992 | Belikan et al. ............. 600/439 |
| 5,103,129 A | 4/1992 | Slayton |
| 5,165,412 A * | 11/1992 | Okazaki ..................... 600/439 |
| 5,443,068 A * | 8/1995 | Cline et al. ................ 600/411 |
| 5,471,988 A | 12/1995 | Fujio |
| 5,520,188 A | 5/1996 | Hennige |
| 5,558,092 A | 9/1996 | Unger |
| 5,762,066 A * | 6/1998 | Law et al. .................. 600/439 |
| 5,769,790 A | 6/1998 | Watkins |
| 5,810,007 A | 9/1998 | Holupka |
| 6,048,323 A * | 4/2000 | Hon ........................... 600/588 |
| 6,050,943 A | 4/2000 | Slayton |
| 6,126,607 A | 10/2000 | Whitmore |
| 6,425,867 B1 | 7/2002 | Vaezy |
| 6,461,314 B1 | 10/2002 | Pant |
| 6,488,639 B1 | 12/2002 | Ribault |
| 6,613,004 B1 | 9/2003 | Vitek |
| 6,645,162 B2 | 11/2003 | Friedman |
| 6,840,936 B2 | 1/2005 | Sliwa |
| 7,063,666 B2 | 6/2006 | Weng |
| 7,258,674 B2 | 8/2007 | Cribbs |
| 7,425,357 B2 | 9/2008 | Lim |
| 7,520,856 B2 | 4/2009 | Vaezy |
| 7,686,763 B2 | 3/2010 | Vaezy |
| 7,695,437 B2 | 4/2010 | Quistgaard |
| 7,753,944 B2 * | 7/2010 | Lacoste et al. ............. 607/96 |
| 7,766,848 B2 * | 8/2010 | Desilets et al. ............ 601/3 |
| 7,993,289 B2 | 8/2011 | Quistgaard |
| 2003/0004439 A1 | 1/2003 | Pant |
| 2003/0171701 A1* | 9/2003 | Babaev ....................... 600/439 |
| 2004/0030268 A1 | 2/2004 | Weng |
| 2004/0153126 A1 | 8/2004 | Okai |
| 2005/0038340 A1 | 2/2005 | Vaezy |
| 2005/0107702 A1 | 5/2005 | He |
| 2005/0154431 A1 | 7/2005 | Quistgaard |
| 2005/0187495 A1 | 8/2005 | Quistgaard |
| 2005/0203399 A1 | 9/2005 | Vaezy |
| 2005/0281444 A1 | 12/2005 | Lundberg |
| 2006/0052701 A1 | 3/2006 | Carter |
| 2007/0238994 A1 | 10/2007 | Stecco |
| 2008/0058683 A1 | 3/2008 | Gifford |
| 2008/0167555 A1* | 7/2008 | Qian et al. .................. 600/439 |
| 2009/0149782 A1* | 6/2009 | Cohen ......................... 601/2 |
| 2009/0171252 A1* | 7/2009 | Bockenstedt et al. ...... 601/2 |
| 2009/0326372 A1 | 12/2009 | Darlington |
| 2010/0023611 A1 | 1/2010 | Yang |
| 2010/0036292 A1 | 2/2010 | Darlington |
| 2010/0049098 A1* | 2/2010 | Shalgi et al. ............... 601/2 |
| 2010/0241005 A1 | 9/2010 | Darlington |

FOREIGN PATENT DOCUMENTS

| | | |
|---|---|---|
| JP | 2005-507750 A | 3/2005 |
| KR | 10-2009-0077694 A | 7/2009 |
| WO | 93/17646 A2 | 9/1993 |
| WO | 00/45706 A1 | 8/2000 |
| WO | 02/100486 A1 | 12/2002 |
| WO | 03/002189 A2 | 1/2003 |
| WO | 2005/000097 A2 | 1/2005 |
| WO | WO 2008/026134 * | 3/2008 ............ A61N 7/02 |
| WO | 2009/097613 A1 | 8/2009 |
| WO | 2010/040140 A2 | 4/2010 |
| WO | WO 2010/040140 A2 * | 4/2010 ............ A61N 7/00 |

OTHER PUBLICATIONS

Delon-Martin, C., et al., "Venous Thrombosis Generation by Means of High-Intensity Focused Ultrasound," Ultrasound in Medicine & Biology 21(1):113-119, 1995.

Friedland, F., "Ultrasonic Therapy," American Journal of Nursing 59(9):1272-1275, Sep. 1959.

Fry, F.J., "Recent Bioeffects With Ultrasound on the Reproductive System and Solid Tumors," Journal of the Acoustical Society of America 63(Suppl. 1):S13, May 1978.

Ngo, F.C., et al., "An Experimental Analysis of a Sector-Vortex Phased Array Prototype," Proceedings of the IEEE Ultrasonics Symposium, Montreal, Oct. 3-6, 1989, vol. 2, pp. 999-1002.

Orsini-Meinhard, K., "UW Tech-Transfer Program Putting Discoveries to Work," The Seattle Times, May 27, 2007, 8 pages.

Sanghvi, N.T., "High Intensity Focused Ultrasound (HIFU) for the Treatment of Rectal Tumors: A Feasibility Study," Proceedings of IEEE Ultrasonics Symposium, Cannes, France, Oct. 31-Nov. 3, 1994, vol. 3, pp. 1895-1898.

ThermoDox™ Animal Studies to Be Presented at 6th International Symposium on Therapeutic Ultrasound in Oxford, England, Aug. 30-Sep. 2, 2006, Celsion, Inc., <http://www.celsion.com/news/releasedetail.dfm> [retrieved Oct. 8, 2007], 2 pages.

"ThermoDox™: Heat-Activated Liposome Drug," © 2007 Celsion, Inc., <http://www.celsion.com/products/ThermoDox.cfm> [retrieved Oct. 8, 2007], 3 pages.

Umemura, S.-I., and C.A. Cain, "Acoustical Evaluation of a Prototype Sector-Vortex Phased-Array Applicator," IEEE Transactions on Ultrasonics, Ferroelectrics, and Frequency Control 39(1):32-38, Jan. 1992.

Vaezy, S., et al., "Image-Guided Acoustic Therapy," Annual Review of Biomedical Engineering 3:375-390 (plus 4 additional pages), Aug. 2001.

Zanelli, C.I., et al., "Design and Characterization of a 10 cm Annular Array Transducer for High Intensity Focused Ultrasound (HIFU) Applications," Proceedings of the IEEE Ultrasonics Symposium, Cannes, France, Oct. 31-Nov. 3, 1994, vol. 3, pp. 1887-1890.

Notice of Reasons for Rejection mailed Mar. 12, 2012, issued in Japanese Patent Application No. 2009-505639, filed Apr. 13, 2007, 7 pages.

International Search Report mailed Mar. 15, 2012, issued in International Application No. PCT/US2011/048331, filed Aug. 18, 2011, 4 pages.

Extended European Search Report mailed Oct. 30, 2015, in corresponding EP 11818816.8.

* cited by examiner

HIFU APPLICATOR

CROSS-REFERENCE TO RELATED APPLICATION

This application claims the benefit of the filing date of U.S. Provisional Application No. 61/375,001, filed Aug. 18, 2010, which is herein incorporated by reference in its entirety.

BACKGROUND

High intensity focused ultrasound (HIFU) is increasingly used for treating internal body tissues of patients in a minimally invasive manner. In order to accurately treat relatively deep tissues such as the uterus, it is generally desirable to increase the size of a HIFU transducer used to produce the HIFU signals in order to achieve desired focal characteristics. On the other hand, it is also important to have a clear acoustic window for delivery of the HIFU signals to the target tissues. For example, in order to maintain a clear acoustic window when treating tissues in the uterus, it is desirable that the applicator fit within an area between the patient's pubic bone and the umbilicus.

Given these competing concerns, there is a need for technology that allows for increasing the size of the HIFU transducer in a HIFU applicator system while managing the size of the footprint of the HIFU applicator.

BRIEF SUMMARY

The following summary introduces a selection of concepts in a simplified form that are further described below in the Detailed Description. This summary is not intended to identify key features of the claimed subject matter, nor is it intended to be used as an aid in determining the scope of the claimed subject matter.

Disclosed herein are embodiments of a HIFU treatment system that is configured to selectively deliver HIFU signals to a treatment volume. The HIFU treatment system includes an applicator that mechanically moves a HIFU transducer to position a focal zone of the transducer in a desired location within the treatment volume.

In at least one embodiment, the HIFU transducer is rotatably connected to a frame by a ball and socket joint. The joint has a center of rotation that is positioned with respect to a maximum diameter of the HIFU transducer such that the HIFU transducer can be physically wobbled to position the focal zone of the HIFU transducer at any desired location within the treatment volume while the HIFU transducer is enclosed in a housing.

In another embodiment, the HIFU transducer is rotatably connected to a frame by an offset gimble assembly that allows the focal zone of the HIFU transducer to be positioned radially outward from the longitudinal axis of the HIFU applicator. The offset gimble assembly provides the HIFU transducer with a center of rotation that is positioned with respect to a maximum diameter of the HIFU transducer such that the HIFU transducer can be physically wobbled to position the focal zone of the HIFU transducer at any desired location within the treatment volume while the HIFU transducer is enclosed in a housing.

In one or more of the foregoing embodiments, the housing of the HIFU applicator has an inner diameter that is not more than 50% larger than the maximum diameter of the HIFU transducer. In another of the foregoing embodiments, the inner diameter of the housing is not more than 30% larger than the maximum diameter of the HIFU transducer. In yet another of the foregoing embodiments, the inner diameter of the housing is not more than 15% larger than the maximum diameter of the HIFU transducer, while in still a further of the foregoing embodiments, the inner diameter of the housing is not more than 10% larger than the maximum diameter of the HIFU transducer.

In one or more of the foregoing embodiments, the mechanism configured to mechanically orient the HIFU transducer is configured such that the focal zone of the HIFU transducer can be positioned over an angle that is at least 5 degrees radially outward from the longitudinal axis of the applicator. In another of the foregoing embodiments, the mechanism is configured such that the focal zone can be positioned over an angle that is at least 10 degrees radially outward from the longitudinal axis of the applicator. In yet another of the foregoing embodiments, the mechanism is configured such that the focal zone can be positioned over an angle that is at least 15 degrees radially outward from the longitudinal axis of the applicator.

In at least one of the foregoing embodiments, the HIFU applicator includes a movable motor plate within the frame. The movable motor plate has two or more linear actuators that selectively move drive shafts that engage the HIFU transducer in order to change the tilt angle of the HIFU transducer relative to the longitudinal axis of the HIFU applicator and therefore adjust the radial position of the focal zone. The movable motor plate also includes a linear actuator that is configured to move the motor plate vertically within the frame in order to adjust the vertical position of the focal zone.

In at least one of the foregoing embodiments, the HIFU transducer further includes an imaging transducer disposed within a central aperture of the HIFU transducer. The imaging transducer has a field of view that includes the treatment volume. The imaging transducer is rotatable around its longitudinal axis to image tissue in the treatment volume in different image planes.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
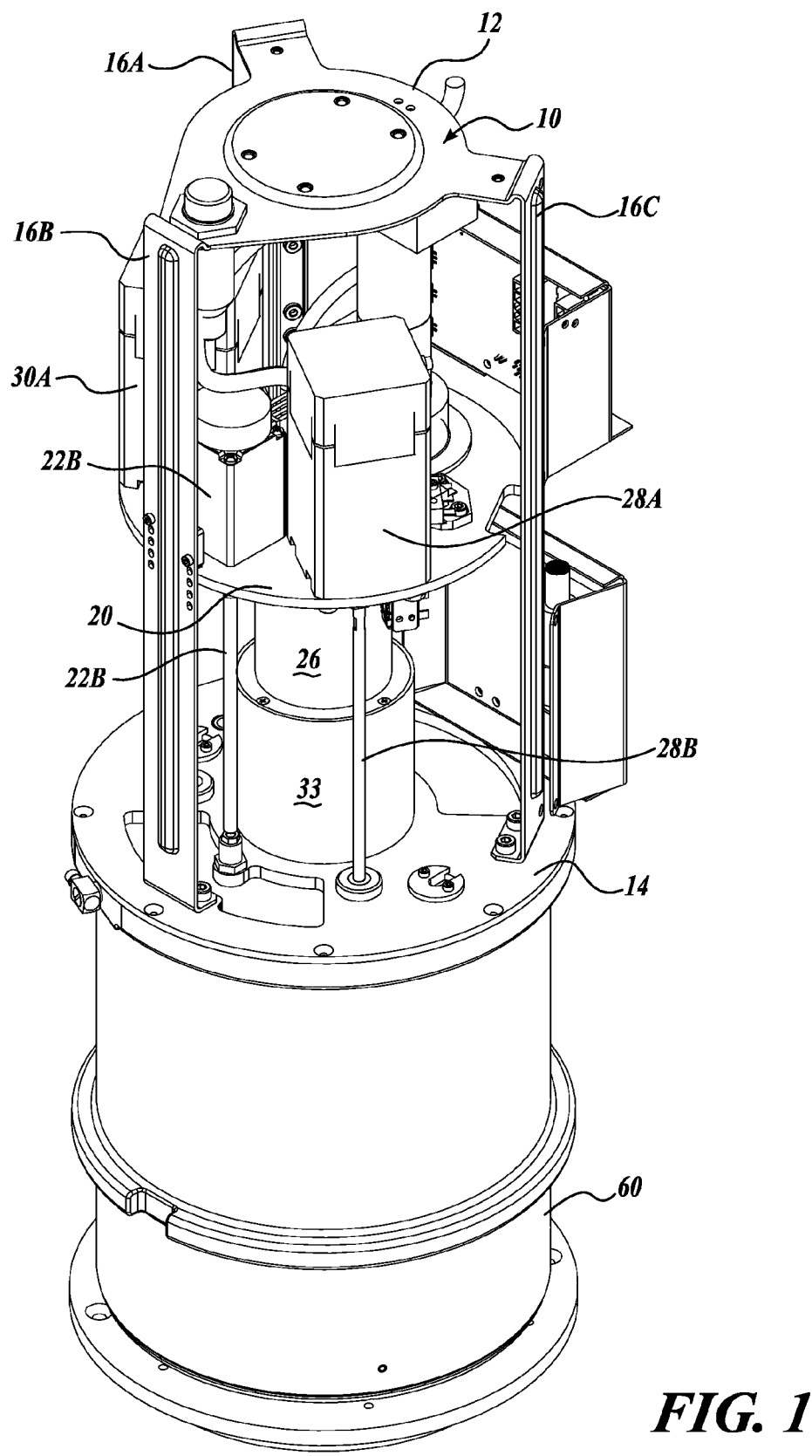
FIG. 1 illustrates a HIFU applicator having a housing positioned over a HIFU transducer in accordance with embodiments of the disclosed technology.

As will be explained in further detail below, the technology described herein relates, at least in part, to a HIFU applicator that has a smaller size footprint for a given transducer size. A smaller size footprint is achieved by locating the center of rotation of the HIFU transducer in the HIFU applicator closer to the plane of the widest dimension of the HIFU transducer. The footprint of a HIFU applicator is typically measured with respect to the transverse inner diameter of the end of the HIFU applicator that is nearest to a treatment volume when providing HIFU therapy. In at least one embodiment, the HIFU applicator further includes an imaging transducer that provides imaging, preferably on center, and preferably includes a wideband receiver that allows harmonics of the HIFU transmit frequency to be detected. In one specific embodiment, for example, the HIFU transducer is an F1 transducer that includes a 12.5 cm diameter ceramic with a minimal aperture cut in the center.

Advantageously, in accordance with the present disclosure, the HIFU applicator may be constructed with a housing that surrounds the HIFU transducer, wherein the housing has an inner dimension that is not more than 50% larger than a maximum diameter of the HIFU transducer. In further embodiments, the inner dimension of the housing may be limited such that the inner dimension is not more than 30% larger than the maximum diameter of the HIFU transducer. In yet other embodiments, the inner dimension of the housing may be further limited so as to be not more than 15% larger than the maximum diameter of the HIFU transducer. In still further embodiments, the inner dimension of the housing may be not more than 10% larger than the maximum diameter of the HIFU transducer. Each of these embodiments has an advantage of limiting the size of footprint of the HIFU applicator while allowing for a larger diameter HIFU transducer.

In any of the various embodiments disclosed herein, the mechanism that is configured to mechanically orient the HIFU transducer may be configured to position the focal zone of the HIFU transducer at least 1.0 cm radially outward from the longitudinal axis of the applicator. Alternatively, in the various embodiments disclosed herein, the mechanism that mechanically orients the HIFU transducer may be configured to position the focal zone of the HIFU transducer at least 2.0 cm radially outward from the longitudinal axis of the applicator. In yet other of the various embodiments disclosed herein, the mechanism that mechanically orients the HIFU transducer may be configured to position the focal zone of the HIFU transducer at least 3.0 cm radially outward from the longitudinal axis of the applicator.

The various embodiments of the HIFU applicator disclosed herein may also be considered in regard to the angular position, or tilt angle, of the HIFU transducer with respect to the longitudinal axis of the applicator. For example, the mechanism that is configured to mechanically orient the HIFU transducer may be configured to position the focal zone of the HIFU transducer over an angle that is at least 5 degrees radially outward from the longitudinal axis of the applicator. Alternatively, in the various embodiments disclosed herein, the mechanism that mechanically orients the HIFU transducer may be configured to position the focal zone of the HIFU transducer over an angle that is at least 10 degrees radially outward from the longitudinal axis of the applicator. In still further embodiments disclosed herein, the mechanism that mechanically orients the HIFU transducer may be configured to position the focal zone of the HIFU transducer over an angle that is at least 15 degrees radially outward from the longitudinal axis of the applicator.

Figure 2:
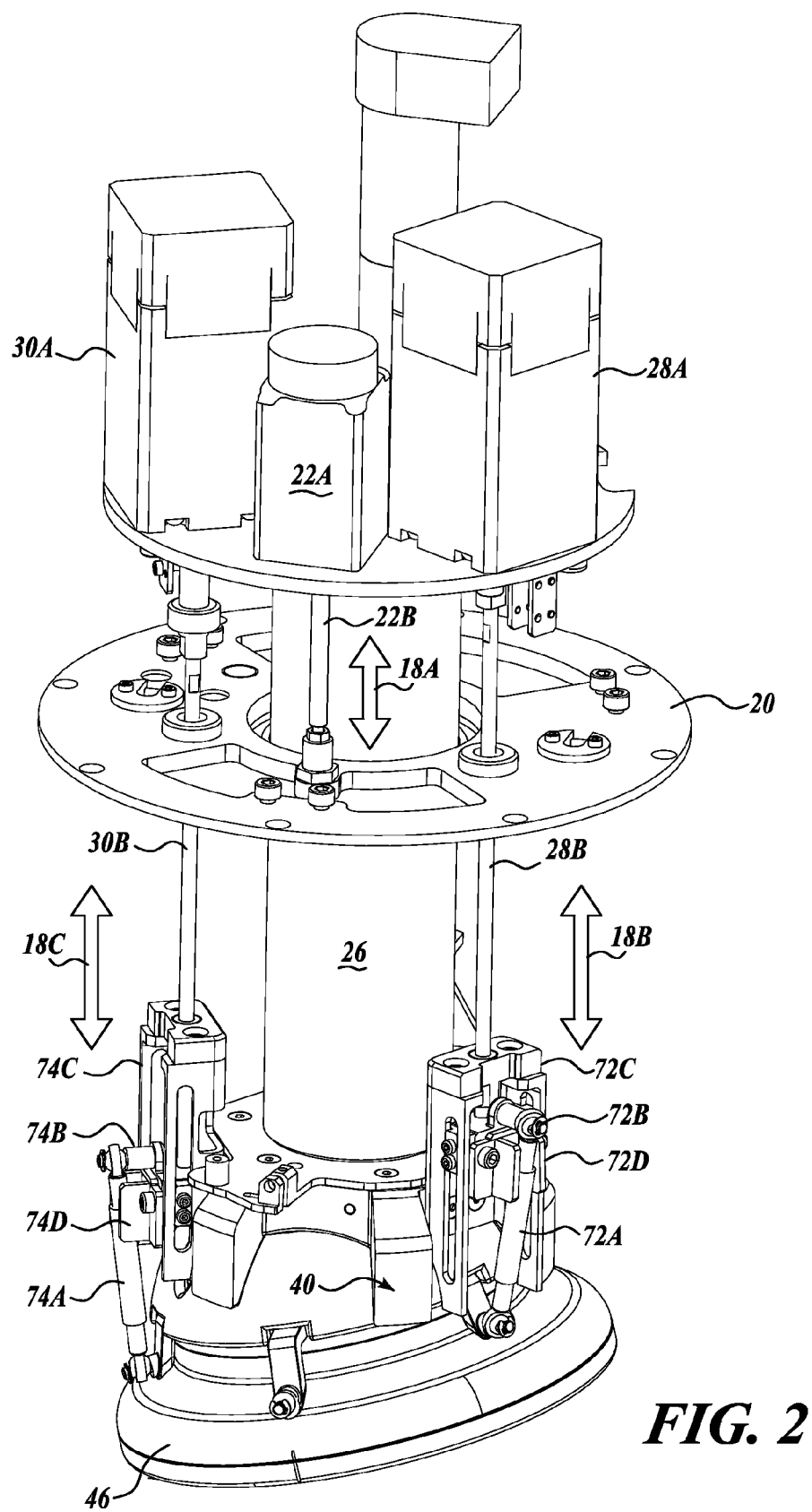
FIG. 2 illustrates the HIFU transducer shown in FIG. 1 with the housing removed.

FIGS. 1 and 2 illustrate major components of at least one embodiment of a HIFU applicator that operates to selectively position a focal zone of a HIFU transducer at a desired location in a treatment volume. The HIFU applicator includes a frame 10 having a fixed top plate 12 that is joined to a fixed base plate 14 by a number of longitudinally extending legs 16A, 16B, 16C. In the embodiment shown, the three legs 16A, 16B, 16C are positioned approximately 120 degrees apart around a circumference of the frame 10, though in other embodiments, greater or fewer legs or different placement of the legs may be used.

Positioned between the top plate 12 and the base plate 14 of the frame is a motor plate 20. Attached to the motor plate 20 are a number of linear actuator motors 22A, 28A, 30A that are configured to adjust the vertical position and angle of a HIFU transducer 46 in order to adjust the position of the HIFU transducer focal zone as will be described below. To adjust the vertical position of the HIFU transducer (and therefore the vertical position of HIFU transducer focal zone), a first linear actuator 22A engages a linear drive shaft 22B. One end of the linear drive shaft 22B is engaged by the linear actuator 22A and the other end of the linear drive shaft 22B is secured to the base plate 14. Activation of the linear actuator 22A causes the motor plate 20 to move up and down within the frame 10 towards or away from the base plate 14 as illustrated by arrow 18A. Secured to the motor plate 20 is a main tube 26 to which a portion of a rotatable joint for orienting the HIFU transducer is secured. In this embodiment, the motor plate 20 and the main tube 26 are interconnected as a rigid structure. The main tube 26 passes through a bearing and a seal 33 on the base plate 14. The main tube 26 supports the HIFU transducer and a portion of a mechanism to orient the HIFU transducer 46 as will be discussed below. Also as will be discussed below, a fluid housing 60 surrounds the HIFU transducer 46. In the embodiments disclosed herein, the longitudinal axis of the HIFU applicator coincides with the longitudinal axis of the main tube 26 (see, e.g., axis 114 shown in FIG. 6).

As shown in the embodiment illustrated in FIG. 2, the HIFU transducer 46 is rotatably secured to an end of the main tube 26. When the motor plate 20 is moved up and down in the frame 10 by the linear actuator 22A, the vertical position of the HIFU transducer 46 is also moved up and down with respect to the frame 10.

In the embodiment shown in FIGS. 1 to 4, the HIFU transducer 46 is rotatably secured to the main tube 26 with a ball and socket joint. In at least one embodiment, the ball and socket joint includes a socket 40 that is secured to an end of the main tube 26. In at least one embodiment, the socket 40 is an annular titanium ring with a number of radially extending arms, the inner surface of which is machined to mate with the outer surface of the ball portion of the joint. The ball portion 44 of the ball and socket joint is a semi-spherical annulus of a polymeric material having a lubricious, convex outer surface that mates with the inner concave surface of the socket 40. The ball 44 is secured to the HIFU transducer 46. Although the embodiment shown has the socket 40 secured to the main tube 26 and the ball 44 secured to the HIFU transducer 46, it will be appreciated that the parts could be reversed such that the ball 44 is secured to the main tube 26 and the socket 40 is secured to the HIFU transducer 46. In other embodiments, different geometries could be used. For example, the socket could be a conical section such that the interface between the ball and socket is a line contact.

In the embodiment shown in FIG. 1, the motor plate 20 also includes a pair of linear actuators 28A, 30A that operate to move two corresponding linear drive shafts 28B, 30B in an upward or downward direction, as illustrated by arrows 18B and 18C. The linear drive shafts 28B, 30B have ends that are coupled to the HIFU transducer 46. As best shown in FIG. 2, the linear drive shafts 28B, 30B are coupled to the HIFU transducer 46 through a pair of linkages 72A, 74A. One end of each linkage is rotatably coupled to a rear surface of the HIFU transducer 46 with a ball joint or other mechanism. The other end of the linkage is coupled to a corresponding movable car 72B, 74B that slides in a corresponding guide 72C, 74C. Each guide 72C, 74C is fixed to the socket 40. One end of each of the drive shafts 28B, 30B is coupled to a corresponding car 72B, 74B such that vertical movement of the linear drive shaft causes the car to slide within the corresponding guide 72C, 74C to move the HIFU transducer 46. The linkages 72A, 74A, the cars 72B, 74B, and the guides 72C, 74C constrain the amount of rotational movement of the HIFU therapy transducer to occur without binding the drive shafts.

It will be appreciated by persons skilled in the art that the described implementation can result in some positional error due to a twisting or other motion of the ball relative to the socket caused by the ball joint on both ends of linkages 72A, 74A. In the current embodiment, this error is controlled to an acceptable level by placing spring element linkage constraints 72D, 74D in the corresponding car 72C, 74C to limit the travel of and bias the lateral position of linkages 72A, 74A.

In an alternative embodiment, the linkages, cars, guides, and linkage constraints are replaced with a flexible link that is rigidly attached at one end to the linear drive shaft 28B, 30B and at the other end to the HIFU transducer 46. In this case, the flexible link would both flex appropriately as the linear drive shafts 28B, 30B are moved and serve to bias the ball relative to the socket thereby minimizing the aforementioned positional error to an acceptable level.

In yet another embodiment, the linkages could be replaced with cables, where the cables wrap on a drum in the fluid side of the base plate 14 and the rotating motor driving the drum is on the dry side of the base plate 14 with seals on the rotating shaft of the motor as the motor shaft passes through the base plate. In this embodiment, the two drive cables and the spring are all in tension, and the two drive cables and the ball-in-socket define the angular position of the HIFU transducer 46.

The position of the linear drive shafts 28B, 30B and the center of rotation of the ball 44 in socket 40 jointly define a plane that is variable to determine the radial position of the focal zone of the HIFU transducer 46. In at least one embodiment, the linear drive shafts 28B, 30B and corresponding linear actuators 28A, 30A are located 120 degrees apart around the circumference of the HIFU transducer 46, though in other embodiments, the drive shafts and corresponding linear actuators may be placed at different circumferential locations. Referring to the embodiment shown in FIG. 2, a spring (not shown) has one end coupled to a rear surface of the HIFU therapy transducer 46 and the other end coupled to the socket 40 to hold the ball 44 in the socket 40 along with the two linkages 72A, 72B. The spring can be a metal coil spring, an elastomeric member, or other material or geometry that serves to provide this function.

Figure 3:
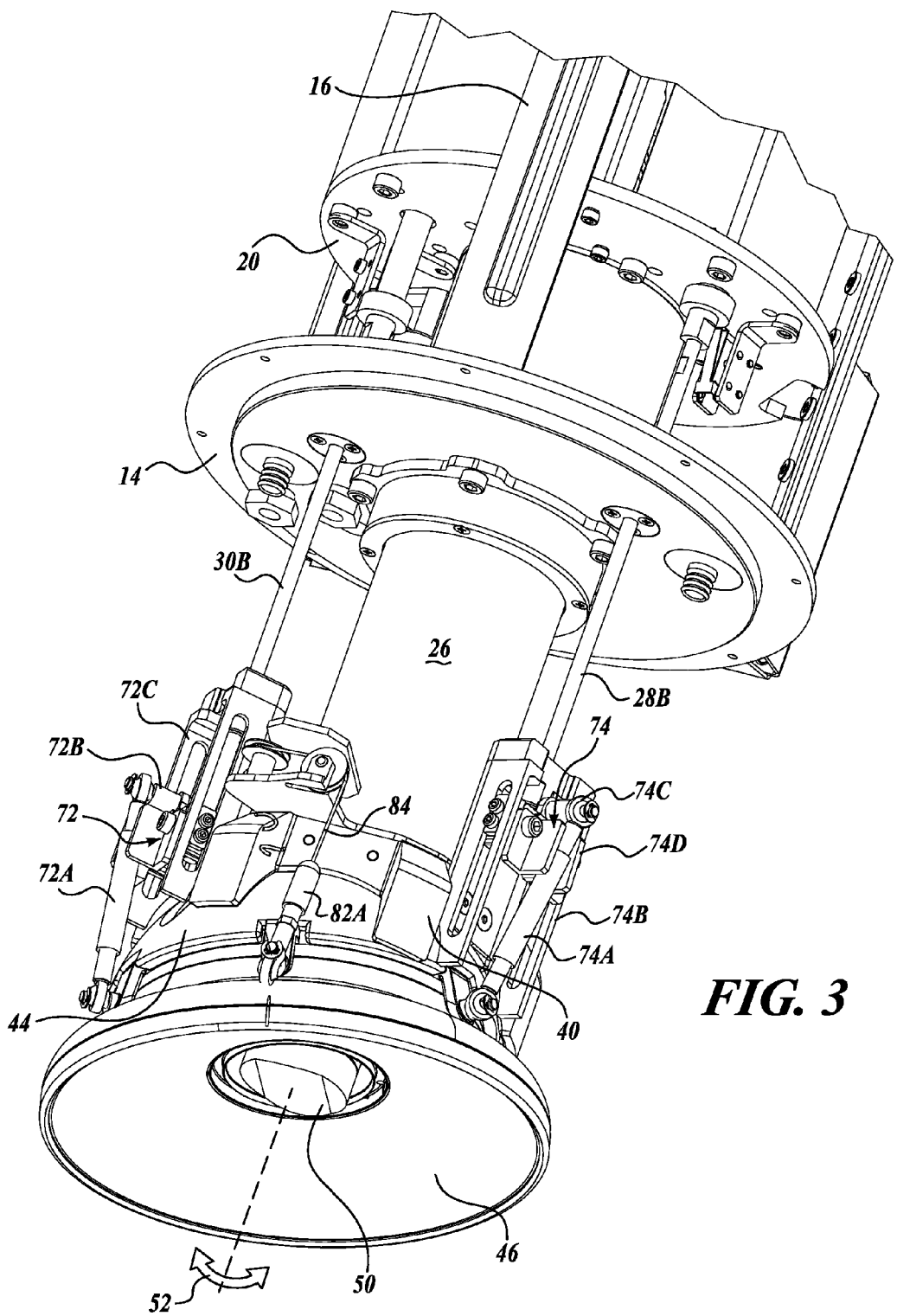
FIG. 3 illustrates further detail of a mechanism to selectively move a ball and socket joint in order to position a focal zone of a HIFU transducer in a desired location in accordance with embodiments of the disclosed technology.

In another embodiment as shown in FIG. 3, a pair of linkages 82A (and 82B out of view) are positioned on opposite sides of the HIFU transducer 46 and have one end coupled to a rear surface of the HIFU transducer 46. The other ends of the linkages 82A, 82B are connected to each other with a cable 84 that is routed through pulleys and a spring (not shown) in line with the cable 84 to hold the ball 44 in the socket 40. In the embodiment shown in FIG. 3, when one of the linkages 82A extends, the other linkage contracts and vise versa.

In yet another embodiment, the spring that helps to hold the ball 44 in the socket 40 is attached to the base plate 14. In yet another embodiment, the spring that holds the ball 44 in socket 40 is attached to the motor plate 20. In still another embodiment, the ball 44 is held in the socket 40 with a linear actuator in force mode.

In at least one embodiment, the linear actuators 28A, 30A are controlled by a computer (not illustrated) such that the linear drive shafts 28B, 30B move out of phase with respect to each other in order to steer the focal zone of the HIFU transducer 46 around a perimeter of a cylindrical elemental treatment volume as HIFU treatment signals are applied as disclosed in U.S. patent application Ser. Nos. 12/573,840 and 12/753,813, which are herein incorporated by reference in their entirety. The linear actuator 22A is controlled by the computer to adjust the vertical position of the focal zone of the HIFU transducer in the treatment volume.

As shown in FIG. 1, a housing 60 surrounds the HIFU transducer 46. To manage the size of the footprint of the HIFU applicator, the center of rotation for the ball and socket joint is positioned near the maximum diameter of the HIFU transducer 46. To treat a volume of tissue within a patient, such as the uterus, it is preferable in at least one embodiment that the HIFU transducer 46 have a diameter of at least 8 cm and more preferably at least 12 cm. In addition, to fit within an acoustic window, such as defined by the area between the patient's pubic bone and the umbilicus, it is desirable that the diameter of the housing be limited, such as to not be more than 15% larger than the maximum diameter of the HIFU transducer and more preferably not more than 10% larger than the maximum diameter of the HIFU transducer. In addition, the HIFU transducer is preferably able to be wobbled up to at least 15 degrees from the longitudinal axis of the applicator.

In the embodiment shown in FIGS. 2 and 3, the HIFU transducer 46 has an F1 aperture with an active area having a diameter of 12.5 cm. With a backing layer and a protective outer rim, the maximum diameter of the HIFU therapy transducer 46 is approximately 13.7 cm. In this particular embodiment, the inner diameter of the housing 60 is approximately 14.8 cm or 8% larger than the maximum diameter of the HIFU treatment transducer while allowing the focal zone of the HIFU therapy transducer to be wobbled up to 4 cm radially or at least 17.75 degrees from the longitudinal axis of the HIFU applicator.

During use, the housing 60 is filled with a liquid, such as degassed water, to provide a good acoustic coupling between the HIFU transducer 46 and the skin of the patient. The front of the housing 60 has a membrane (not shown) made of Dupont Kapton™ or other flexible material that allows the front face of the HIFU applicator to make good contact with the skin of the patient and to allow good acoustic transmission. The base plate 14 of the frame includes a number of seals where wiring for the HIFU transducer 46, the linear actuator shafts 28B, 30B, and the main tube 26 that supports HIFU transducer 46 pass through the base plate 14. The seals prevent the liquid from leaking out of the housing 60.

As is best shown in FIG. 3, the HIFU applicator also includes an imaging transducer 50 that is disposed in-line with the longitudinal axis of the HIFU applicator. The imaging transducer 50 extends through the main tube 26 and through a central aperture in the ball and socket joint and the HIFU transducer. The imaging transducer 50 has a field of view that extends over the range of positions where the focal zone of the HIFU transducer 46 can be positioned. A motor and gear (not shown) on the motor plate 20 may be activated to selectively rotate the imaging transducer 50 about its longitudinal axis, as illustrated by arrow 52, to change the plane of the imaging transducer. In at least one embodiment, the motor and gear can move the imaging transducer in an arc of 180 degrees to allow for a 3D imaging, for sweeping through the target volume, or to select an arbitrary image plane. In at least one embodiment, the imaging transducer 50 is rotated back and forth over an angle of 90 degrees to capture images of the tissue being treated in two orthogonal planes. A pressure sensor 80 (see FIG. 4) may be configured to monitor the fluid pressure to allow the computer to automatically adjust the fluid volume as the linear actuator 22A adjusts the vertical position of the HIFU transducer 46.

In another embodiment, the imaging transducer 50 may be placed on the perimeter of the HIFU applicator rather than the center. In such a case, the imaging transducer may be a single ring array or a conventional imaging array duplicated around the perimeter for bi-plane imaging (2 transducers), with a split aperture (4 transducers), and/or a transducer that is mechanically moved around the perimeter for full volumetric or multiplane imaging as disclosed in U.S. patent application Ser. No. 12/165,346, which is herein incorporated by reference.

Figure 4:
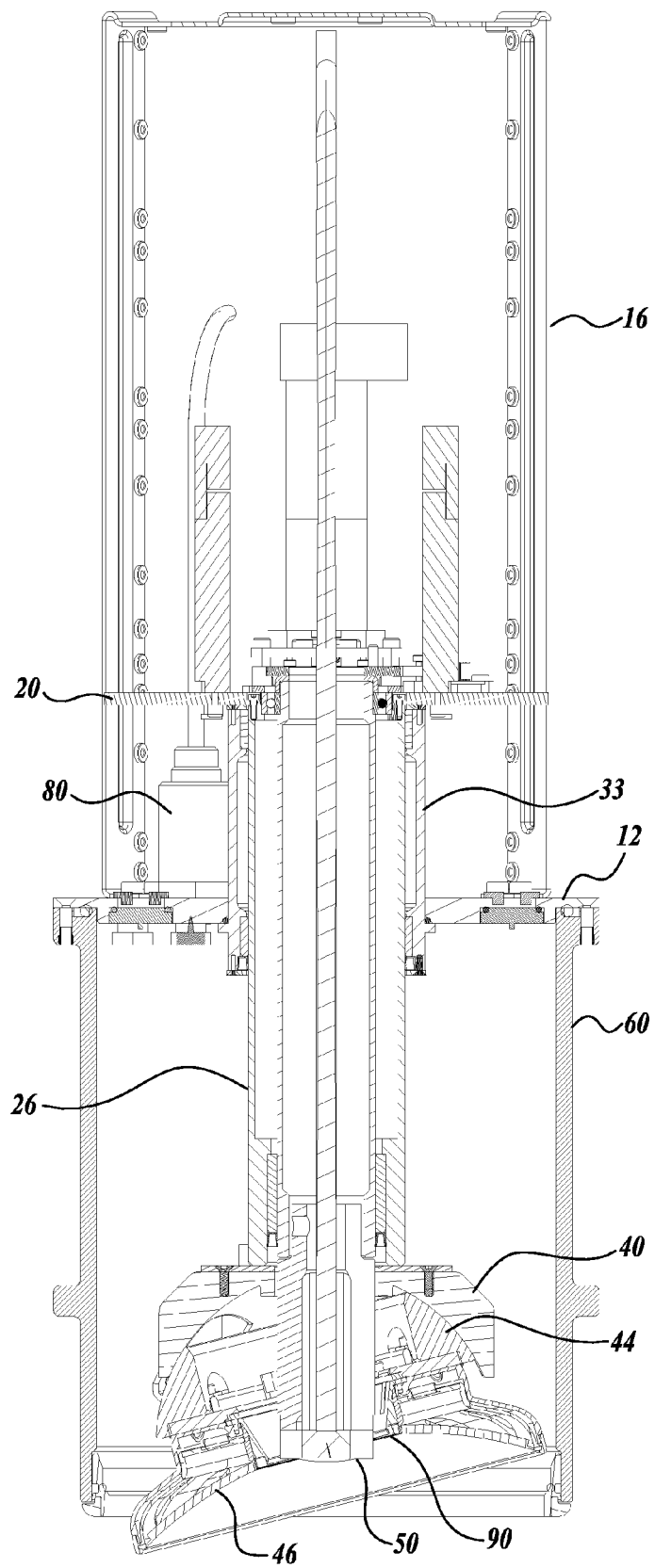
FIG. 4 illustrates a cross-section of a HIFU applicator in accordance embodiments of the disclosed technology.

As shown in FIG. 4, the HIFU applicator may also include a wideband transducer 90 such as a PVDF transducer for receiving HIFU signals reflected from the tissue. The wideband transducer can detect harmonics of the HIFU transmit frequency to perform output compensation as disclosed in U.S. patent application Ser. No. 12/537,217, which is herein incorporated by reference. In the embodiments herein, the wideband transducer 90 follows the HIFU transducer 46.

FIGS. 5 to 8 illustrate major components of another embodiment of a HIFU applicator that operates to selectively position a focal zone of a HIFU transducer at a desired location in a treatment volume. As with the embodiment shown in FIGS. 1 to 4, the HIFU applicator in FIGS. 5 to 8 includes a frame 10 having a fixed top plate 12 joined to a fixed base plate 14 by longitudinally extending legs 16A, 16B, 16C. A motor plate 20 is positioned between the top plate 12 and the base plate 14. Linear actuator motors 22A, 28A, 30A are attached to the motor plate 20 and are configured to adjust the vertical position and angle of a HIFU transducer 46 to adjust the position of the HIFU transducer focal zone. A first linear actuator 22A engages a linear drive shaft 22B to adjust the vertical position of the HIFU transducer. A main tube 26 is secured to the motor plate 20 and passes through a bearing and a seal 33 on the base plate 14. The main tube 26 supports the HIFU transducer and a portion of a mechanism that orients the HIFU transducer 46 relative to the treatment volume. The main tube 26 has a longitudinal axis 114 (FIG. 6) that, in the embodiments disclosed herein, coincides with the longitudinal axis of the HIFU applicator.

Positioned between the top plate 12 and the base plate 14 of the frame is a motor plate 20. Attached to the motor plate 20 are linear actuator motors that adjust the vertical position and angle of a HIFU transducer in order to adjust the position of the HIFU transducer focal zone. To adjust the vertical position of the focal zone, the first linear actuator 22A engages a linear drive shaft 22B. One end of the linear drive shaft 22B is engaged by the linear actuator 22A and the other end of the linear drive shaft 22B is secured to the base plate 14. Activation of the linear actuator 22A causes the motor plate 20 to move up and down within the frame 10 towards or away from the base plate 14.

Secured to the motor plate 20 is a main tube 26. The motor plate 20 and the main tube 26 are interconnected as a rigid structure. The main tube 26 passes through a bearing and a seal 33 on the base plate 14. The main tube 26 supports the HIFU transducer and a offset gimble assembly 104 that operates to orient the HIFU transducer 46. The HIFU transducer 46 is rotatably secured to the end of the main tube 26.

In the embodiment shown in FIGS. 5 to 8, the HIFU transducer 46 is rotatably secured to the main tube 26 by a single sided offset gimble comprised of an offset gimble pivoting mount arm 104A that is rotatably affixed by a pivot link 104C to an offset gimble swing arm 104B. The offset gimble pivoting mount arm 104A is rotatably affixed to the lower end of the main tube 26 by an annular bearing set 105. The offset gimble pivoting mount arm 104A is therefore constrained to only rotate about a longitudinal centerline axis 114 of the main tube 26. The offset gimble swing arm 104B is rotatably affixed to the HIFU transducer 46 by a pivot link 104D.

Figure 5:
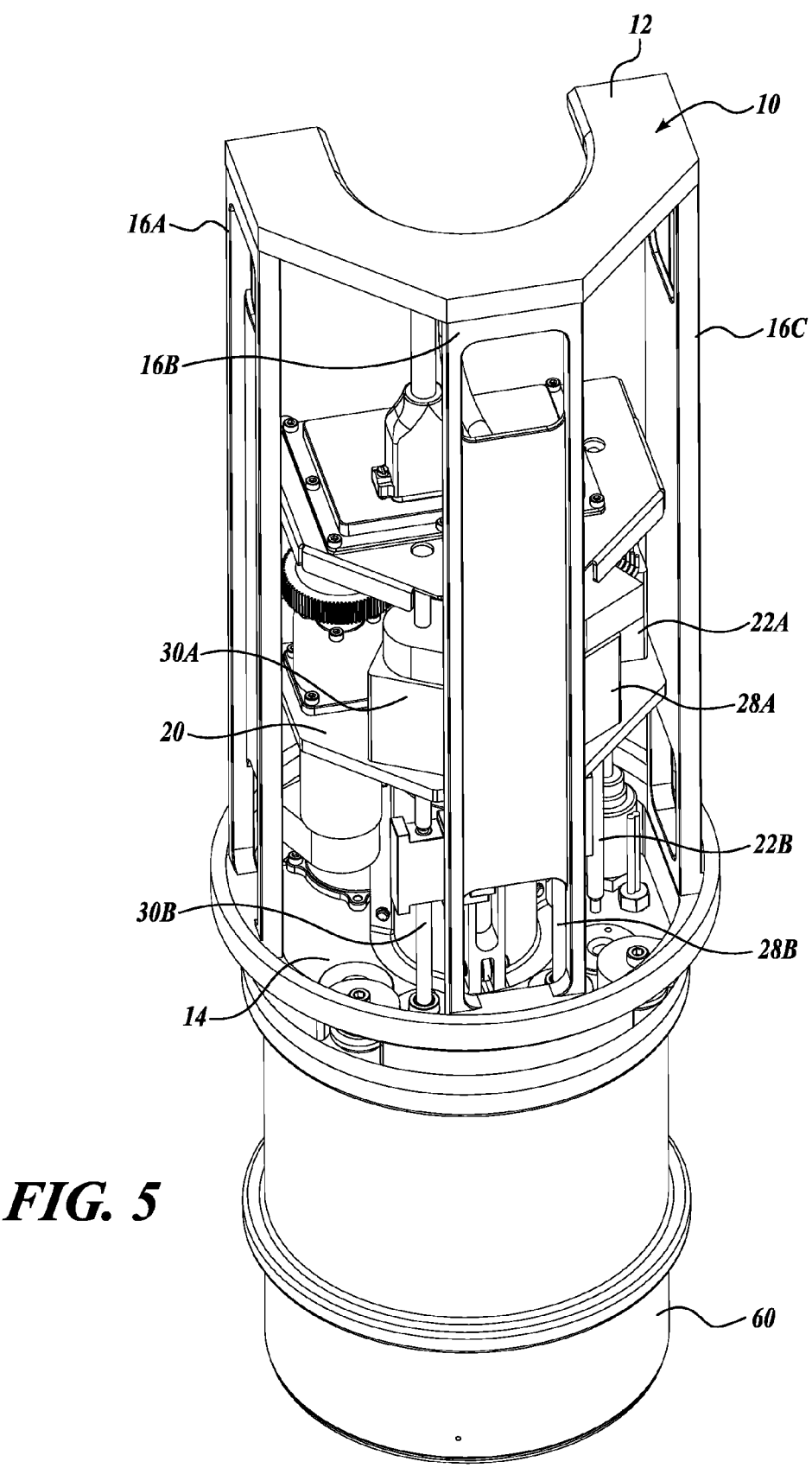
FIG. 5 illustrates another embodiment of the disclosed technology including a HIFU applicator having a housing positioned over a HIFU transducer.

Referring to FIG. 5, the offset gimble assembly 104 as illustrated has a primary gimble pivot axis 116 that is defined by the angle of the pivot axis of the pivot link 104C at the end of the offset gimble pivoting mount arm 104A to pass through the main tube 26 centerline axis 114. The primary gimble pivot axis 116 passes through the centerline axis 114 at the defined center of rotation of the HIFU transducer 46. At the primary gimble pivot axis, the center of rotation of the HIFU transducer 46 will be constant for all orientations of the offset gimble pivoting mount arm 104A.

The HIFU transducer 46 is attached to the end of the offset gimble pivoting mount arm 104A through the single sided offset gimble swing arm 104B. A secondary gimble pivot axis 118 of the gimble mechanism is defined by the pivot axis of the pivot link 104D. The offset gimble swing arm 104B houses a bearing set at both ends whose rotational axes are constrained to pass through the defined center of rotation of the HIFU transducer 46. Therefore, the center of rotation of the HIFU transducer 46 through the secondary gimble pivot axis 118 will be constant for all orientations of both the offset gimble pivoting mount arm 104A and the offset gimble swing arm 104B. The offset gimble assembly 104 constrains the movement of the HIFU transducer 46 to maintain a constant centerpoint of rotation for all available orientations.

Figure 6:
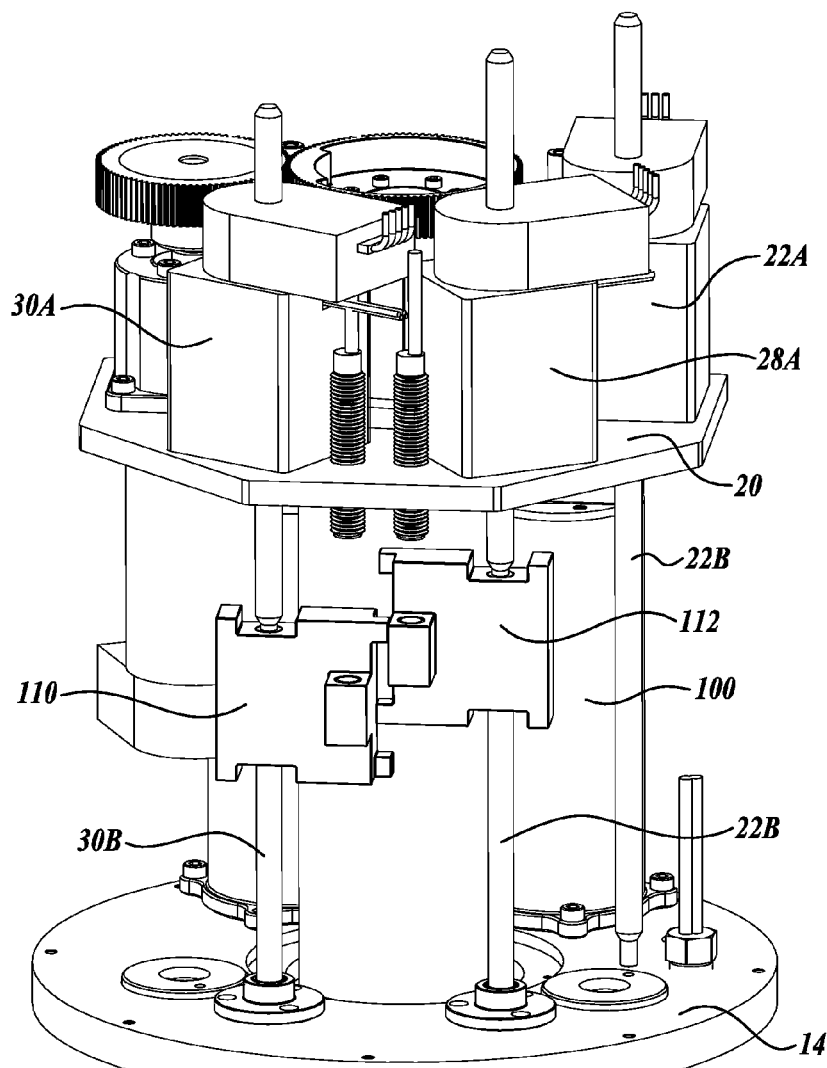
FIG. 6 illustrates the HIFU transducer shown in FIG. 5 with the housing removed.
Figure 6:
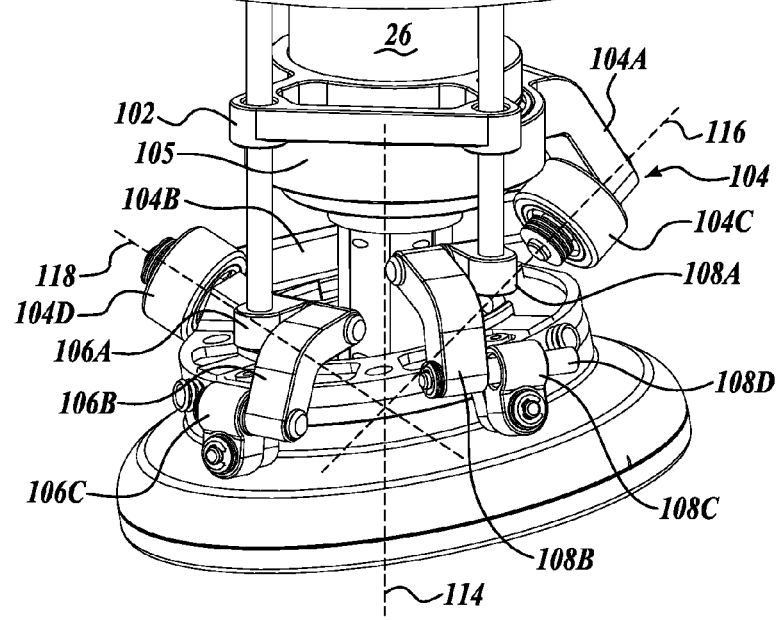
Figure 7:
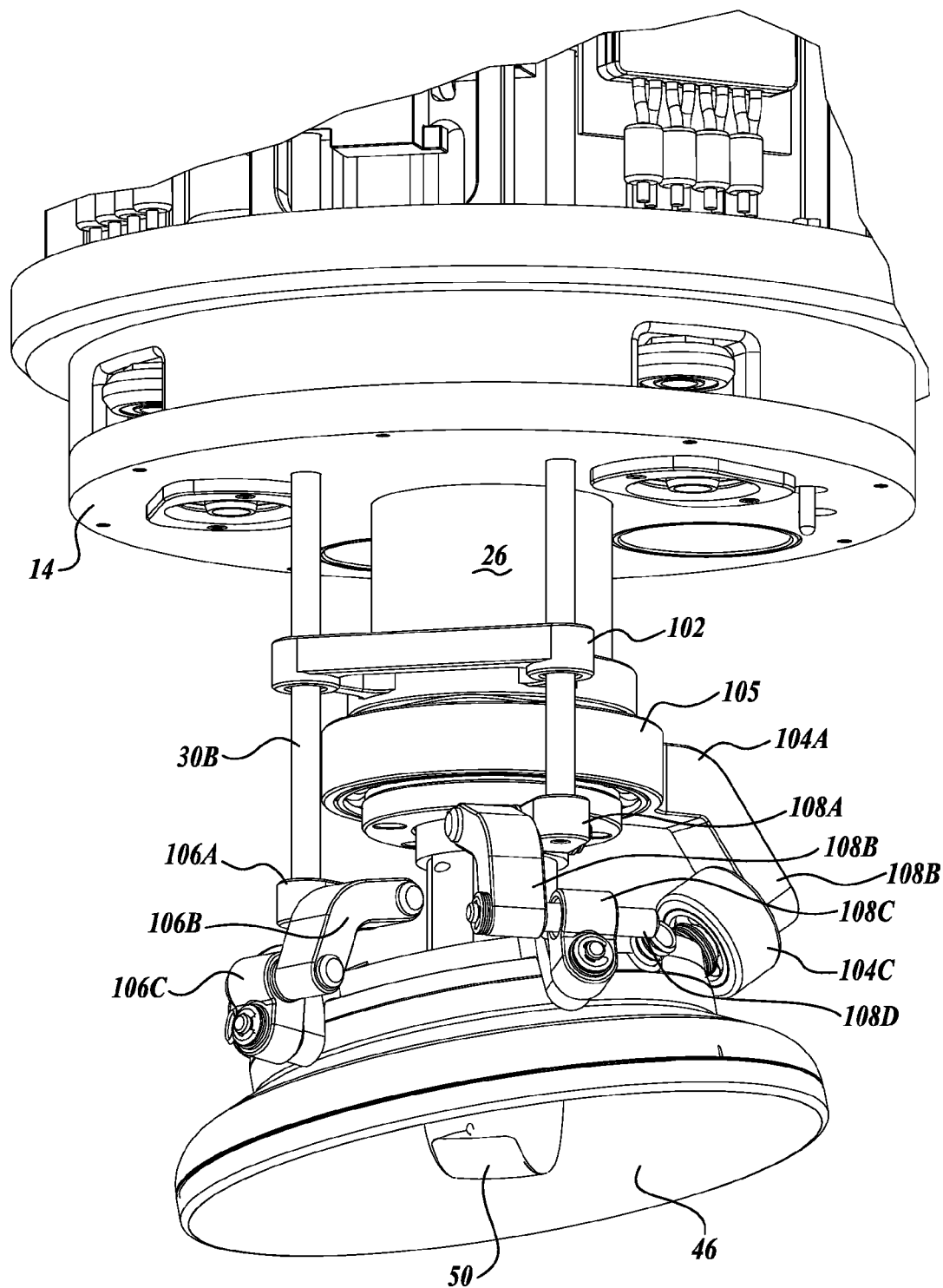
FIG. 7 illustrates further detail of the embodiment shown in FIGS. 5 and 6, with an offset gimble assembly that selectively positions a focal zone of a HIFU transducer in a desired location.

As with the embodiments shown in FIGS. 1 to 4, the embodiments shown in FIGS. 5 to 8 include a pair of linear actuators 28A, 30A that move a corresponding pair of linear drive shafts 28B, 30B having ends that are coupled to the HIFU transducer 46. As best shown in FIG. 6, the linear drive shafts 28B, 30B are coupled to the HIFU transducer 46 through a pair of linkages 106, 108. One end of the drive shaft 30B is coupled to a corresponding drive linkage 106 at a drive link pivot 106A.

The drive linkage 106 is comprised of the drive link pivot 106A, a drive compensation link 106B, and a drive link biaxial pivot, such that vertical movement of the linear drive shaft 30B causes the corresponding drive compensation link 106B to pivot between the drive link pivot 106A and the corresponding drive link biaxial pivot 106C. This pivoting of the drive compensation link 106B dynamically adjusts the combined effective length of the drive shaft 30B and the drive linkage 106 in order to linearize the relationship between the translation distance of the drive shaft 30B and the rotation angle of the HIFU transducer 46 throughout the range of motion of the drive shaft 30B. Movement of the drive linkage 106 is constrained to a plane that passes through the centerline axes of the drive shaft 30B and the main tube 26 by linear bearings within the base plate 14 and the extended linear bearing guide 102 that is affixed to the end of the main tube 26, effectively restricting rotation of the HIFU transducer 46 about the centerline axis 114 of the main tube 26.

Similarly, one end of the drive shaft 28B is coupled to a corresponding drive linkage 108. The drive linkage 108 is comprised of a drive link pivot 108A, a drive compensation link 108B, and a drive link biaxial pivot 108C, such that vertical movement of the linear drive shaft 28B causes the corresponding drive compensation link 108B to pivot between the drive link pivot 108A and the corresponding drive link biaxial pivot 108C. The drive linkage 108 operates similar to the drive linkage 106 with the addition that the drive linkage 108 allows for dynamic changes in horizontal separation distance between the two pivots 106C and 108C that connect the HIFU transducer 46 to the drive linkages 106 and 108. The drive linkage 108 allows for such dynamic changes in horizontal separation distance by the addition of a drive link linear glide shaft 108D and a corresponding linear bearing in a linear glide of the drive link bi-axial pivot 108C. The drive link linear glide shaft 108D is able to slide within the linear glide of the bi-axial pivot 108C along the longitudinal axis of the glide shaft 108D.

The linear actuators 28A, 30A may be controlled by a computer (not shown) such that the linear drive shafts 28B, 30B move out of phase with respect to each other in order to steer the focal zone of the HIFU transducer 46 around the perimeter of a cylindrical elemental treatment volume as HIFU treatment signals are applied, e.g., as disclosed in U.S. patent application Ser. Nos. 12/573,840 and 12/753,813. The computer can control the linear actuator 22A to adjust the vertical position of the focal zone of the HIFU transducer in the treatment volume.

As shown in FIG. 5, a fluid housing 60 surrounds the HIFU transducer 46. To manage the size of the footprint of the HIFU applicator, the HIFU applicator includes a single sided offset gimble as shown in FIGS. 5 to 8 which positions the center of rotation of the HIFU transducer 46 near the maximum diameter of the HIFU transducer 46.

As with earlier described embodiments, the HIFU transducer 46 shown in FIGS. 5 and 6 may have a maximum diameter of approximately 13.7 cm. If the inner diameter of the housing 60 is approximately 14.8 cm, the housing will have a diameter that is 8% larger than the maximum diameter of the HIFU transducer.

During use, the housing 60 is filled with a fluid, such as degassed water, that is maintained within the housing by a membrane cap (e.g., made of Dupont Kapton™ or other flexible material) stretched across the lower front of the housing 60. The fluid provides a good acoustic coupling at a patient interface between the HIFU transducer 46 and the skin of the patient.

Figure 8:
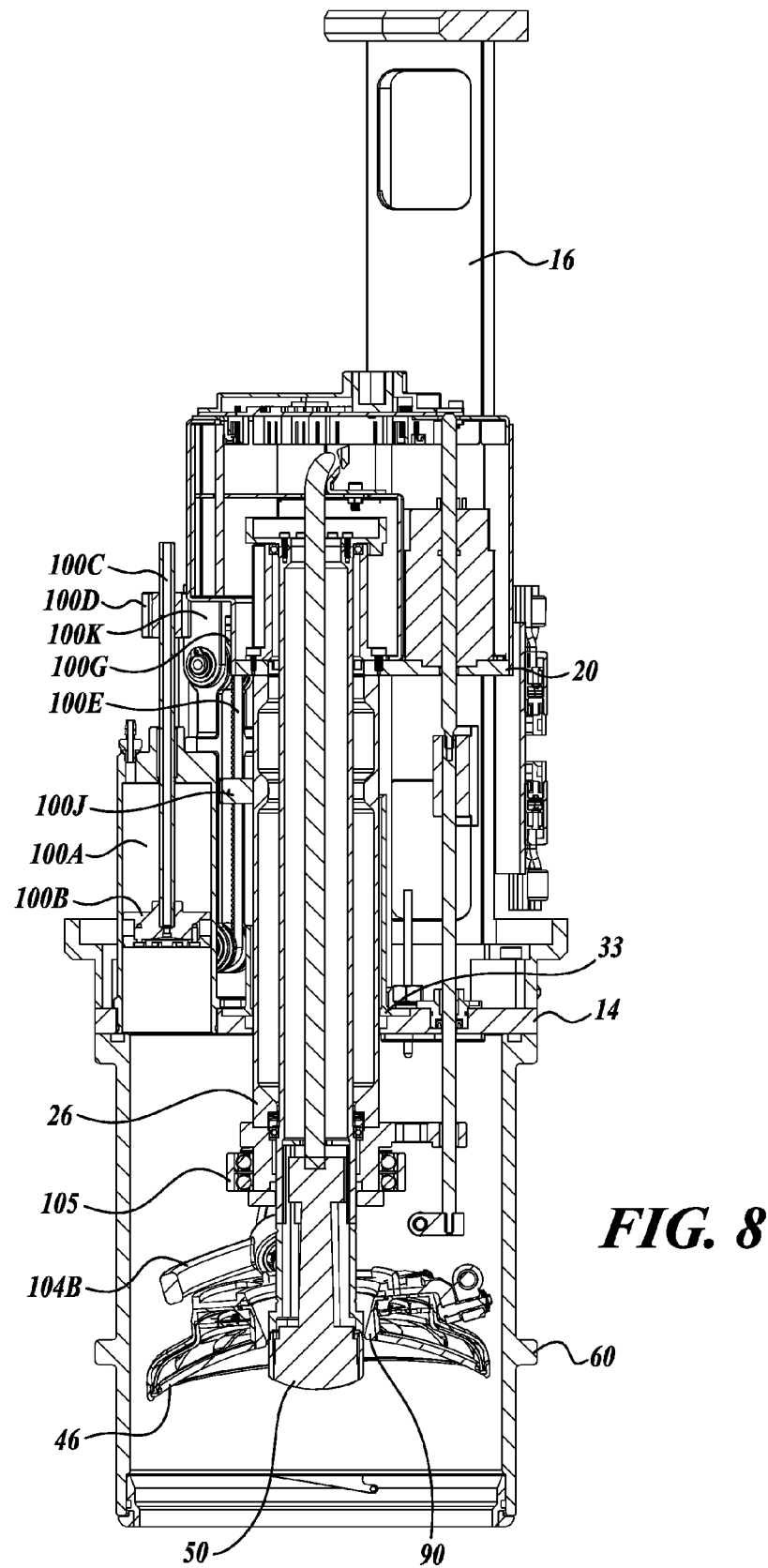
FIG. 8 illustrates a cross-section of the embodiment shown in FIGS. 5 and 6 in accordance with embodiments of the disclosed technology.
Figure 9:
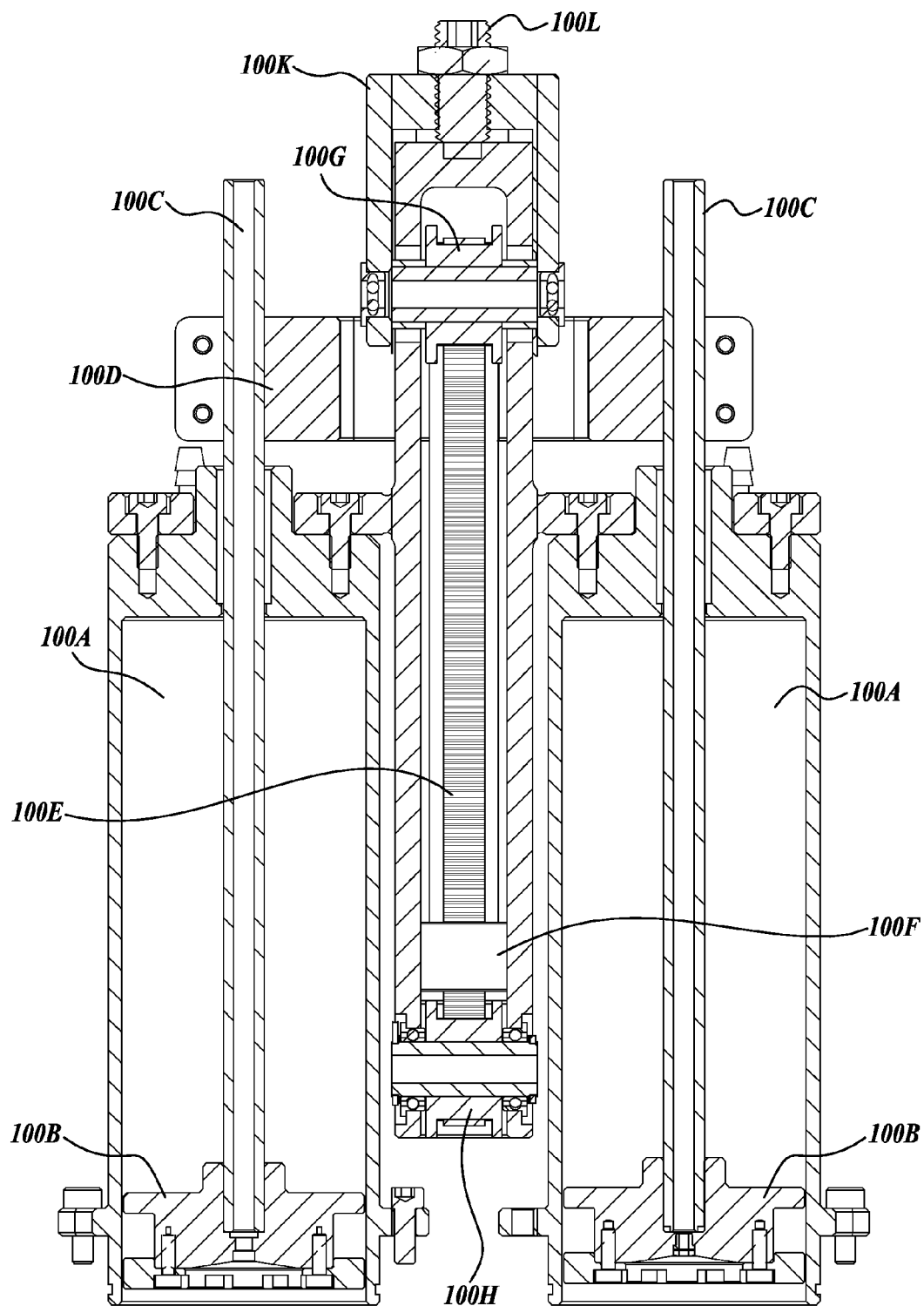
FIG. 9 illustrates a mechanical fluid volume compensation system in accordance with embodiments of the disclosed technology.

As the main tube 46 translates toward and away from the patient interface, the volume of fluid within the fluid housing 60 decreases and increases respectively. A mechanical fluid volume compensation system 100, referred to herein as "FVCS," is therefore provided to account for this dynamic change in fluid volume. The fluid volume compensation system 100 is coupled to the fluid housing 60 and includes one or more cylinders that can fill with fluid from the housing 60 such that the combined volume of the housing 60 and the fluid-filled portions maintains a constant fluid volume. Referring to FIGS. 8 and 9, a pair of hydraulic pistons 100B are positioned within FVCS cylinders 100A. The hydraulic pistons 100B are coupled to the main tube 26 in an inverse relationship via a FVCS belt 100E. The FVCS belt 100E is mounted on fixed lower idler pulley 100H and an adjustable upper idler pulley 100G tensioned by a FVCS belt tensioner 100K. In at least one embodiment, the tension of the FVCS belt 100E is adjusted by rotating a bolt or set screw 100L. After adjustment, the bolt or screw 100L may be secured in place by a corresponding nut.

The main tube 26 is attached to one side of the FVCS belt 100E by means of a tube side belt clamp 100J. The FVCS pistons 100B are driven by FVCS drive shafts 100C which are attached to the opposite side of the belt 100E through a FVCS drive shaft bridge 100D and a bridge side belt clamp 100F.

In combination, the two FVCS pistons 100B have the same cross sectional area as the main tube 26. As the main tube 26 travels upward (thus elevating the HIFU transducer 46 away from the patient interface), the two FVCS pistons 100B travel downward at the same rate. This one-to-one inverse coupling of the matched cross sectional area of the main tube 26 and the two FVCS pistons 100B passively and effectively eliminates most if not all of the fluid volume change during translation of the main tube 26.

Depending on the needs of the HIFU applicator system, the volume within the cylinders 100A beneath the pistons 100B may be dynamically adjusted to accommodate changes in the volume of fluid in the housing 60 that occur, for example, over multiple uses of the HIFU applicator system. The HIFU applicator system may include one or more actuators that are coupled to the drive shafts 100C to adjust the initial position the FVCS pistons 100B within their respective cylinders 100A to achieve desired changes in the combined volume of the housing 60 and the cylinders 100A beneath the pistons 100B. The system may also include one or more sensors that monitor changes in the fluid volume, e.g., by monitoring the fluid pressure in the housing 60 or by monitoring the tension of the membrane cap at the patient interface. Signals from the sensors may be fed back to a computer that interprets the fluid conditions within the housing 60 and, as needed, causes the actuators to adjust the steady state position of the pistons 100B within the cylinders 100A as discussed above.

While the fluid volume compensation system 100 is illustrated in FIGS. 8 and 9 as being incorporated into the HIFU applicator shown in FIGS. 5 and 6, it will be appreciated that the FVCS 100 may be incorporated into other embodiments of the HIFU applicator, including the embodiments shown in FIGS. 1 to 4.

In FIGS. 10 to 13, simplified representations of the linkages 106, 108 are provided for further clarity of understanding. The drive link pivots 106A, 108A are represented as pivot point E. The drive link biaxial pivot 106C and the drive link biaxial pivot 108C (with linear glide) are represented as pivot point F. The drive compensation links 106B, 108B are represented by a single line extending between pivot points E and F that is allowed to pivot at points E and F. The drive shafts 30B, 28B, attached to the drive compensation links 106B, 108B at pivot point E, are represented by a single line that is only allowed to move up and down. The HIFU transducer 48 is represented by a single line that is allowed to pivot at both point F and the HIFU transducer's center point of rotation D.

Figure 13:
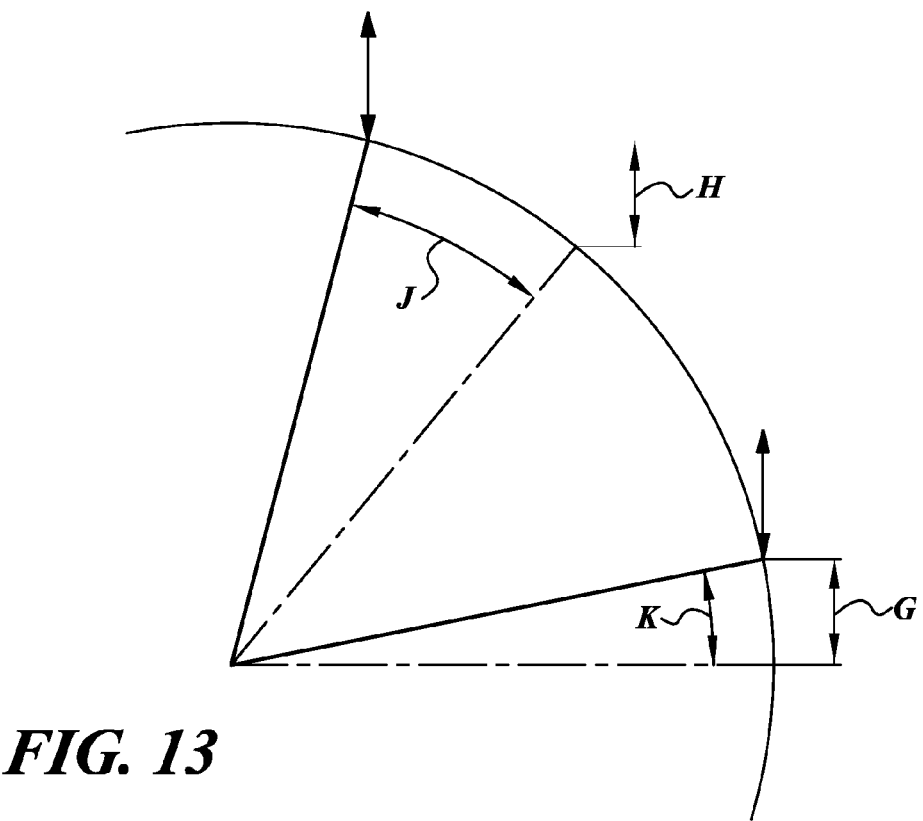

The location of pivot point F on the HIFU transducer and the location of drive shafts 30B, 28B as well as the length of compensation links 106B, 108B have been optimized to best linearize the relationship between the drive shaft 30B, 28B translation distance B and the HIFU transducer tilt angle C. As shown in FIG. 13, the vertical component of the distance traveled G, H around a circle is not linearly related to the angle traveled K, J. It is shown in FIG. 13 that although the vertical distances traveled G, H are the same, the angle K is much smaller than angle J. It is this nonlinearity that the drive compensation links 106B, 108B make close to linear in the linkages 106, 108.

Figure 10:
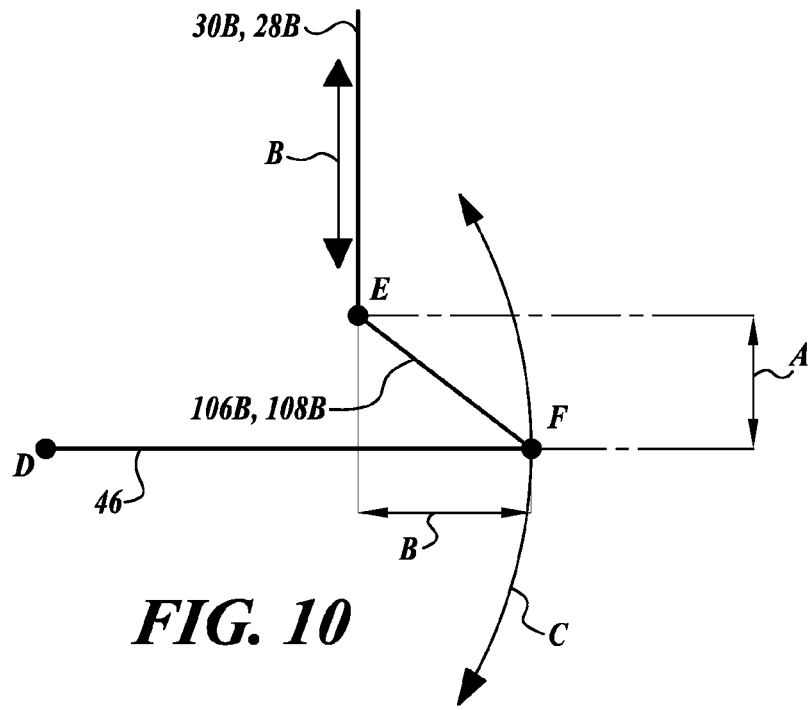
FIGS. 10 to 13 illustrate simplified representations of linkages used in the embodiment shown in FIGS. 5 and 6.
Figure 11:
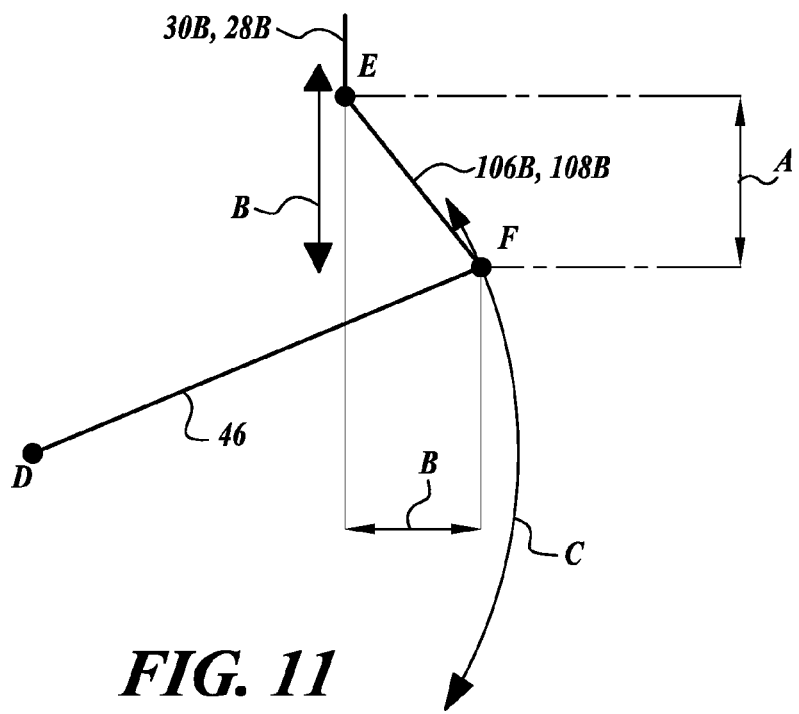
Figure 12:
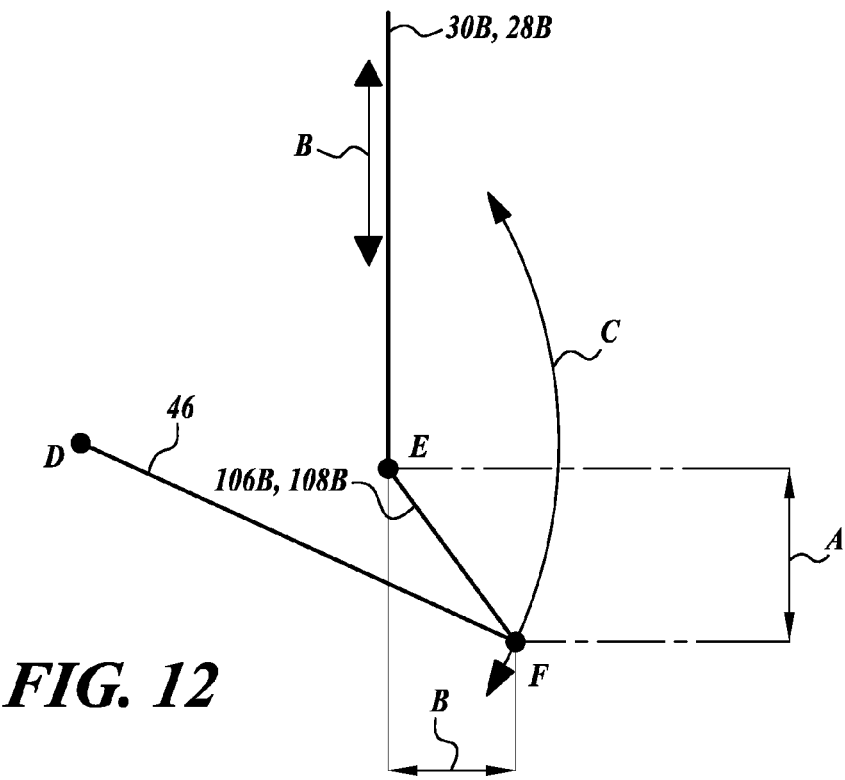

In FIG. 10, the simplified representation of the HIFU transducer 46 is shown in a horizontal position. As the drive shafts 30B, 28B are driven upward (FIG. 11) or downward (FIG. 12), the drive compensation links 106B, 108B are driven upward (FIG. 11) or downward (FIG. 12) about pivot point E. Since the other end of the drive compensation links 106B, 108B is constrained to pivot only about point F on the HIFU transducer 46, and the HIFU transducer 46 can only pivot about point D, the drive compensation links must rotate towards vertical as the HIFU transducer is tilted up or down off of horizontal (FIG. 10). It is this dynamic rotation of drive compensation links 106B, 108B that causes the vertical distance A to increase and the horizontal distance B to decrease as the HIFU transducer 46 is tilted up or down off of horizontal (FIG. 10). As the distance B is reduced, the rate of change of the angle C of HIFU transducer 46 is increased, linearizing the ratio of the displacement B of the drive shafts 30B, 28B and the tilt C of the HIFU transducer 46.

It is notable that the HIFU applicator system shown above is not an over constrained system nor is it under constrained system, but is a fully constrained system. In other words, the position of the HIFU transducer 46 and therefore the position of the focal zone of the transducer within the treatment volume can always be determined by the relative displacement of the drive shafts 28B, 30B.

While illustrative embodiments have been illustrated and described, it will be appreciated that various changes can be made therein without departing from the scope of the invention. For example, although certain disclosed embodiments use imaging ultrasound to image the tissue being treated, it will be appreciated that other embodiments may use different imaging systems, such as magnetic resonance imaging (MRI). In addition, the applicator is not limited to use in treating uterine tissues. The applicator could be used to treat other internal body tissues such as the breast, prostate, kidneys, liver, etc.

The embodiments of the invention in which an exclusive property or privilege is claimed are defined as follows:

1. A HIFU applicator configured to deliver high intensity focused ultrasound (HIFU) signals to a treatment volume, comprising:
   a frame;
   a HIFU transducer movably coupled to the frame and configured to deliver HIFU treatment signals to a focal zone;
   a mechanism configured to mechanically orient the HIFU transducer with respect to the frame such that the focal zone of the HIFU transducer can be positioned radially outward from a longitudinal axis of the HIFU applicator, wherein the mechanism includes a plurality of movable drive shafts, each drive shaft being connected to a linkage that couples the HIFU transducer to the drive shaft, and wherein at least one of the linkages coupling the HIFU transducer to a drive shaft is not axially aligned with the longitudinal axis of the HIFU applicator; and
   a housing surrounding the HIFU transducer, wherein the HIFU transducer has a maximum diameter in a transverse plane defined across the HIFU transducer, and wherein the housing has an inner diameter that is not more than 50% larger than the maximum diameter of the HIFU transducer,
   wherein the mechanism configured to mechanically orient the HIFU transducer provides the HIFU transducer with a center of rotation that is located substantially at the transverse plane of the HIFU transducer, and
   wherein, when the HIFU transducer is oriented in a centered position in which the transverse plane of the HIFU transducer is perpendicular to the longitudinal axis of the HIFU applicator, the focal zone of the HIFU transducer is positioned within the treatment volume approximately inline with the longitudinal axis of the HIFU applicator.

2. The HIFU applicator of claim 1, further comprising a mechanism configured to selectively raise and lower the HIFU transducer to vertically position the focal zone of the HIFU transducer with respect to the frame.

3. The HIFU applicator of claim 1, wherein the mechanism configured to mechanically orient the HIFU transducer comprises a joint having rotatable ball and socket, wherein the ball is connected to one of the frame or the HIFU transducer and the socket is connected to the other of the frame or the HIFU transducer.

4. The HIFU applicator of claim 3, wherein the plurality of drive shafts engage the HIFU transducer via the linkages to selectively move the ball with respect to the socket.

5. The HIFU applicator of claim 3, wherein the ball and socket joint rotatably couples the HIFU transducer to the frame such that the HIFU transducer can be physically tilted to position the focal zone in a direction radially outward from the longitudinal axis of the HIFU applicator; and
   wherein the ball and socket joint provides the HIFU transducer with a center of rotation that is located with respect to the maximum diameter of the HIFU transducer such that the focal zone of the HIFU transducer can be radially oriented up to 4 cm away from the longitudinal axis of the HIFU applicator at a depth of at least 10 cm while the housing surrounding the HIFU transducer has an internal diameter that is not more than 10% larger than the maximum diameter of the HIFU transducer.

6. The HIFU applicator of claim 1, wherein the mechanism configured to mechanically orient the HIFU transducer comprises a single sided offset gimble assembly that couples the HIFU transducer to the frame and allows the focal zone of the HIFU transducer to be positioned radially outward from the longitudinal axis of the HIFU applicator, wherein the single sided offset gimble assembly includes an offset gimble pivoting mount arm that is rotatably affixed by a pivot link to an offset gimble swing arm, and the offset gimble swing arm is rotatably affixed by a pivot link to the HIFU transducer.

7. The HIFU applicator of claim 6, wherein the plurality of drive shafts engage the HIFU transducer via the linkages to move the HIFU transducer relative to the frame within constraints of the single sided offset gimble assembly and orient the HIFU transducer at an angular position relative to the longitudinal axis of the HIFU applicator.

8. The HIFU applicator of claim 7, wherein the linkages are drive linkages that dynamically adjust the combined effective length of the respective drive shaft and the drive linkage to linearize the relationship between a translation distance of the drive shaft and the angular position of the HIFU transducer.

9. The HIFU applicator of claim 1, wherein the HIFU transducer has a central aperture and the applicator includes an imaging transducer positioned within the central aperture.

10. The HIFU applicator of claim 9, wherein the mechanism configured to mechanically orient the HIFU transducer is configured to physically move the HIFU transducer relative to the imaging transducer in order to change the radial position of the focal zone in the treatment volume.

11. The HIFU applicator of claim 1, wherein the mechanism configured to mechanically orient the HIFU transducer with respect to the frame is configured such that the focal zone of the HIFU transducer can be positioned at least 1.0 cm radially outward from the longitudinal axis of the applicator.

12. The HIFU applicator of claim 1, wherein the mechanism configured to mechanically orient the HIFU transducer with respect to the frame is configured such that the focal zone of the HIFU transducer can be positioned at least 2.0 cm radially outward from the longitudinal axis of the applicator.

13. The HIFU applicator of claim 1, wherein the inner diameter of the housing is not more than 30% larger than the maximum diameter of the HIFU transducer.

14. The HIFU applicator of claim 1, wherein the inner diameter of the housing is not more than 15% larger than the maximum diameter of the HIFU transducer.

15. The HIFU applicator of claim 1, wherein the inner diameter of the housing is not more than 10% larger than the maximum diameter of the HIFU transducer.

16. The HIFU applicator of claim 1, wherein the mechanism for mechanically orienting the HIFU transducer is configured such that the focal zone of the HIFU transducer can be positioned over an angle that is at least 5 degrees radially outward from the longitudinal axis of the applicator.

17. The HIFU applicator of claim 1, wherein the mechanism for mechanically orienting the HIFU transducer is configured such that the focal zone of the HIFU transducer can be positioned over an angle that is at least 10 degrees radially outward from the longitudinal axis of the applicator.

18. The HIFU applicator of claim 1, wherein the mechanism for mechanically orienting the HIFU transducer is configured such that the focal zone of the HIFU transducer can be positioned over an angle that is at least 15 degrees radially outward from the longitudinal axis of the applicator.

19. The HIFU applicator of claim 1, wherein the frame includes a main tube that is configured to translate vertically toward and away from the treatment volume and the housing surrounding the HIFU transducer includes fluid, wherein a volume of the fluid within the housing changes as the main tube vertically translates, and wherein the HIFU applicator further comprises a fluid volume compensation system that is configured to mechanically maintain a constant fluid volume for the HIFU applicator, the fluid volume compensation system including one or more cylinders, each cylinder having a hydraulic piston disposed therein that is coupled to the main tube in an inverse relationship such that as the main tube translates downward, the hydraulic pistons translate upward, providing portions of the one or more cylinders that fill with fluid and adjust for most if not all of the fluid volume change in the housing resulting from translation of the main tube.

20. The HIFU applicator of claim 19, further comprising one or more actuators that are coupled to corresponding drive shafts of the hydraulic pistons, wherein the one or more actuators are configured to adjust the position of the hydraulic pistons within their respective cylinders to maintain a constant combined fluid volume in the housing and the fluid-filled portions of the one or more cylinders.

21. The HIFU applicator of claim 1, wherein the housing surrounding the HIFU transducer is cylindrical.

22. A HIFU applicator configured to deliver high intensity focused ultrasound (HIFU) signals to a treatment volume, comprising:

a frame;

a HIFU transducer movably coupled to the frame and configured to deliver HIFU treatment signals to a focal zone, wherein the HIFU transducer has a transverse axis defined transversely across the HIFU transducer; and a mechanism configured to mechanically orient the HIFU transducer with respect to the frame such that the focal zone of the HIFU transducer can be positioned radially outward from a longitudinal axis of the HIFU applicator, wherein the mechanism provides the HIFU transducer with a center of rotation that is located away from an inner surface of the HIFU transducer within a volume surrounded by the HIFU transducer, and wherein, when the HIFU transducer is oriented in a centered position in which the transverse axis of the HIFU transducer is perpendicular to the longitudinal axis of the HIFU applicator, the focal zone of the HIFU transducer is positioned within the treatment volume approximately inline with the longitudinal axis of the HIFU applicator.

23. A HIFU applicator configured to deliver high intensity focused ultrasound (HIFU) signals to a treatment volume, comprising:

a frame;

a HIFU transducer movably coupled to the frame and configured to deliver HIFU treatment signals to a focal zone; and a mechanism configured to mechanically orient the HIFU transducer with respect to the frame such that the focal zone of the HIFU transducer can be positioned radially outward from a longitudinal axis of the HIFU applicator, wherein the mechanism provides the HIFU transducer with a center of rotation that is located substantially at a plane defined transversely across the HIFU transducer at a maximum diameter of the HIFU transducer, and wherein, when the HIFU transducer is oriented in a centered position in which the plane defined transversely across the HIFU transducer is perpendicular to the longitudinal axis of the HIFU applicator, the HIFU transducer is positioned to deliver the HIFU treatment signals to the focal zone approximately inline with the longitudinal axis of the HIFU applicator.

24. A HIFU applicator configured to deliver high intensity focused ultrasound (HIFU) signals to a treatment volume, comprising:

a frame;

a HIFU transducer movably coupled to the frame and configured to deliver HIFU treatment signals to a focal zone;

a mechanism configured to mechanically orient the HIFU transducer with respect to the frame such that the focal zone of the HIFU transducer can be positioned radially outward from a longitudinal axis of the HIFU applicator, wherein the mechanism includes a plurality of movable drive shafts, each drive shaft being connected to a linkage that couples the HIFU transducer to the drive shaft, and wherein at least one of the linkages coupling the HIFU transducer to a drive shaft is not axially aligned with the longitudinal axis of the HIFU applicator; and a housing surrounding the HIFU transducer, wherein the housing has an inner diameter that is not more than 50% larger than a maximum diameter of the HIFU transducer, wherein the mechanism configured to mechanically orient the HIFU transducer comprises a single sided offset gimble assembly that couples the HIFU transducer to the frame and allows the focal zone of the HIFU transducer to be positioned radially outward from the longitudinal axis of the HIFU applicator, wherein the single sided offset gimble assembly includes an offset gimble pivoting mount arm that is rotatably affixed by a pivot link to an offset gimble swing arm, and the offset gimble swing arm is rotatably affixed by a pivot link to the HIFU transducer.

25. The HIFU applicator of claim 24, wherein the plurality of drive shafts engage the HIFU transducer via the linkages to move the HIFU transducer relative to the frame within constraints of the single sided offset gimble assembly and orient the HIFU transducer at an angular position relative to the longitudinal axis of the HIFU applicator.

26. The HIFU applicator of claim 25, wherein the linkages are drive linkages that dynamically adjust the combined effective length of the respective drive shaft and the drive linkage to linearize the relationship between a translation distance of the drive shaft and the angular position of the HIFU transducer.

* * * * *